United States Patent
Ignagni (10) Patent No.: US 8,273,039 B1
(45) Date of Patent: Sep. 25, 2012

(54) APPARATUS FOR CLEARING MUCUS FROM THE PULMONARY SYSTEM

(75) Inventor: Mario Ignagni, Brooklyn Park, MN (US)

(73) Assignee: Mario Ignagni, Brooklyn Park, MN (US)

( * ) Notice: Subject to any disclaimer, the term of this patent is extended or adjusted under 35 U.S.C. 154(b) by 884 days.

(21) Appl. No.: 12/319,169

(22) Filed: Dec. 31, 2008

Related U.S. Application Data (63) Continuation-in-part of application No. 11/803,257, filed on May 14, 2007, now Pat. No. 7,927,293.

(51) Int. Cl.
*A61H 1/00* (2006.01)
*A61H 7/00* (2006.01)
*A61H 19/00* (2006.01)

(52) U.S. Cl. .......................... 601/151; 601/46; 601/150

(58) Field of Classification Search .................... 601/46, 601/48, 71, 41–44, 148–152
See application file for complete search history.

(56) References Cited

U.S. PATENT DOCUMENTS

| | | | |
|---|---|---|---|
| 3,955,563 A | 5/1976 | Maione | |
| 4,838,263 A | 6/1989 | Warwick et al. | |
| 5,235,967 A | 8/1993 | Arbisi et al. | |
| 5,569,170 A | 10/1996 | Hansen | |
| 5,924,448 A * | 7/1999 | West | 137/565.13 |
| 6,036,662 A * | 3/2000 | Van Brunt et al. | 601/41 |
| 6,190,337 B1 | 2/2001 | Nedwell | |
| 6,736,785 B1 | 5/2004 | Van Brunt | |
| 6,958,046 B2 | 10/2005 | Warwick et al. | |
| 7,096,866 B2 | 8/2006 | Be'eri et al. | |
| 7,416,536 B2 | 8/2008 | DeVlieger | |
| 7,927,293 B1 * | 4/2011 | Ignagni et al. | 601/46 |
| 2002/0111571 A1 * | 8/2002 | Warwick et al. | 601/44 |
| 2004/0158177 A1 * | 8/2004 | Van Brunt et al. | 601/44 |
| 2007/0239087 A1 * | 10/2007 | Kivisto | 601/44 |

* cited by examiner

*Primary Examiner* — Kristen Matter (57) ABSTRACT

An apparatus for clearing mucus from the pulmonary system, utilizing two different types of external excitation applied concurrently to the thorax, the first type of excitation consisting of vibrational stimulations, and the second type of excitation consisting of compressive stimulations, with control means provided to regulate the excitations.

15 Claims, 5 Drawing Sheets

APPARATUS FOR CLEARING MUCUS FROM THE PULMONARY SYSTEM

CROSS REFERENCE TO PRIOR APPLICATION

This application is a continuation-in-part of U.S. patent application Ser. No. 11/803,257, entitled "Means For Clearing Mucus From The Pulmonary System", filed May 14, 2007, now U.S. Pat. No. 7,927,293 B1, issued Apr. 19, 2011.

FIELD OF THE INVENTION

The invention generally relates to the use of mechanical stimulation of the thorax to promote clearance of mucus from the lungs and trachea.

BACKGROUND OF THE INVENTION

A number of diseases can lead to severe impairment of normal lung functioning. Among these are: Cystic Fibrosis, Emphysema, and Immotile Celia Syndrome. Cystic Fibrosis is a hereditary disease that leads to the accumulation of large quantities of viscous mucus in the lungs. Emphysema causes impairment of the lung's ability to clear mucus as a result of damage to the celia, the small hair-like vibrating appendages covering the lung wall that loosen and help propel the mucus out of the lung; and damage to the alveoli, the small air sacs covering the lung surface, which are instrumental in coughing mucus out of the lungs. Immotile Celia Syndrome is a hereditary disease in which the normal functioning of the celia is absent or impaired, leading to the accumulation of mucus in the lungs. In all of these diseases, mucus retained in the lungs becomes a natural breeding ground for harmful bacteria that can cause repeated bouts of serious infections, as well as leading to decreased respiratory gas exchange.

In addition to drugs and inhalants, various physical therapies may be applied to assist in expelling mucus from the pulmonary system. In particular, patients may undergo chest percussion by a trained physical therapist to loosen lung mucus, which is followed by postural drainage and coughing to expel the mucus from the lungs. This can be a time consuming and discomforting therapy which meets with only limited success, especially if the patient is in a weakened condition.

More recently, high-frequency chest compression techniques have been employed as a means of eliminating the need for a physical therapist, and to improve effectiveness of mucus clearance from the lungs. Such techniques have been taught by Warwick and Hansen, U.S. Pat. No. 4,838,263; U.S. Pat. No. Hansen, 5,569,170; and Warwick and Hansen, U.S. Pat. No. 6,958,046. High-frequency chest compression, as applied by an inflatable vest, has been shown in clinical trials and in actual use to be efficacious in clearing mucus from the lungs. However, a patient may require 2 to 3 hours of treatment each day to keep the lungs relatively free of mucus.

The present invention addresses the need for a more effective approach to clearing mucus from the pulmonary system that will reduce physical stress to the body, and require less time in the daily regimen of treatment.

BRIEF SUMMARY OF THE INVENTION

A first controllable excitation source applies vibrational stimulations directly to the thorax which, in turn, causes the pulmonary system to develop small-amplitude sympathetic vibrations, thereby loosening the mucus attached to the lungs and trachea. A second independently controllable excitation source applies compressive stimulations to the patient just below the rib cage, leading to upward thrusts of the thoracic diaphragm. Since the lungs rest directly on the thoracic diaphragm, localized motions of the lung walls will be initiated at the points of contact. This causes the air in the lungs to experience pressure and flow-rate pulsations which, in turn, cause the mucus attached to the lungs and trachea to be propelled in incremental steps toward the mouth. Control means are provided to insure that efficacious pulmonary system vibration and thoracic compressions are achieved without undue stress to the patient. The use of two separately controllable thoracic excitation sources offers greater potential for optimization than a single excitation, as applied by existing high-frequency chest compression techniques, and may have advantages in size, cost, mucus clearance rate, and reduced physical stress to the body.

DETAILED DESCRIPTION OF THE INVENTION

Figure 1:
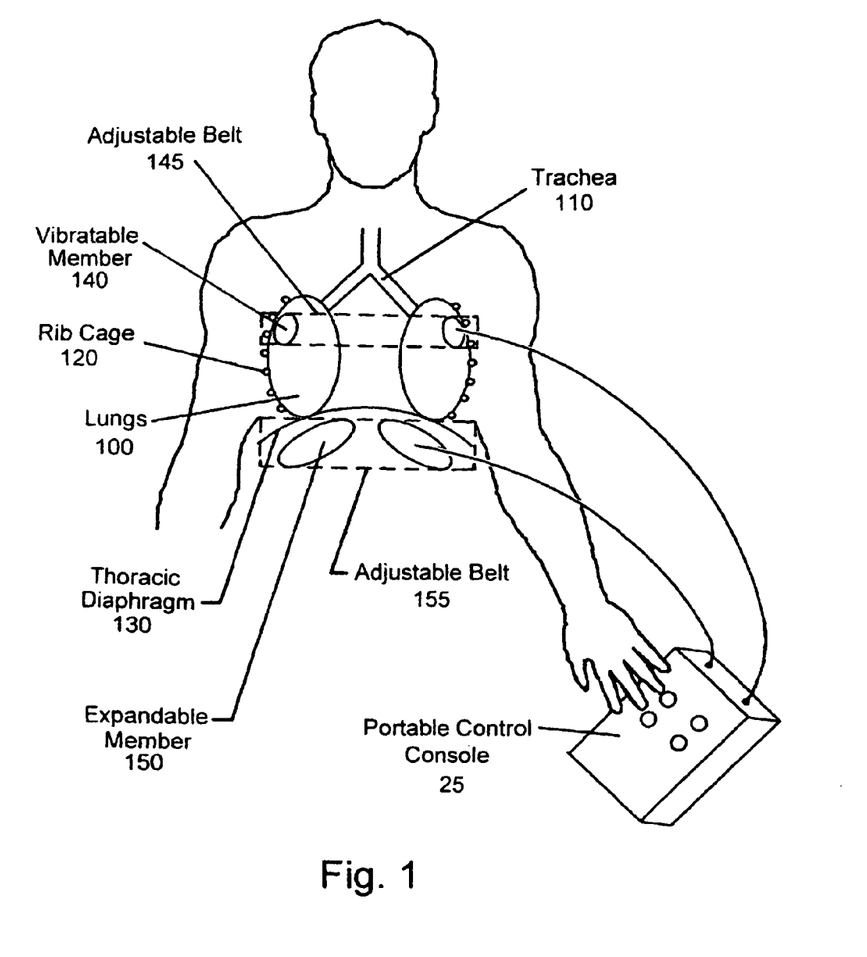
FIG. 1 illustrates the parts of the body which are affected by the external excitations, and the sources of the excitations.

FIG. 1 illustrates the concept for clearing the lungs 100 and trachea 110 of mucus. The concept is based on the employment of two separately controllable excitations, in combination, to maximize the effectiveness of mucus clearance from the pulmonary system. The first excitation augments the action of the cilia by inducing sustained low-amplitude high-frequency vibrations in the lungs 100.

This serves to create continuous oscillatory translational motions of the lung wall relative to the mucus which, in turn, expedites movement of the mucus. Vibration of the lung walls is achieved by employing at least one vibratable member 140 held in contact with the thorax. From a physical perspective, the lung wall behaves essentially like a perfect elastic membrane, while the mucus does not. Accordingly, because the lung wall and mucus respond differently in a vibrational environment, relative motion will occur between them, which creates a boundary layer of lower viscosity mucus adjacent to the lung wall, thereby increasing mucus mobility.

Given that sustained vibration of the lung wall expedites the movement of mucus, the second function of propelling the mucus along the lung wall is achieved by mechanically pumping the air in the lungs 100 utilizing compressive stimulations of the lower thorax, characterized by a much higher amplitude and lower frequency than the vibrational stimulations. Compression of the lower thorax is achieved by employing at least one expandable member 150 held in contact with the thorax, which leads to upward thrusts of the thoracic diaphragm 130. The pressure and flow-rate variations of the air enclosed within the lungs 100, induced by the upward thrusts of the thoracic diaphragm, create the motive forces required to propel the mucus in incremental steps toward the mouth, where it can be swallowed or expectorated.

The first excitation means for applying vibrational stimulations to the thorax can take various forms. In one exemplary application, the vibrational stimulations could be applied by one or more mechanical vibrators which transmit inertial reaction forces to the thorax. In still another exemplary application, the vibrational stimulations could be applied by sonic waves originating from one or more audio speakers. In yet another exemplary application, the vibrational stimulations could be applied by an inflatable pneumatic belt or cuff that causes oscillatory compressive forces to be transmitted to the thorax. More than one vibration-generating device would typically be utilized, with vibration applied symmetrically to the thorax, allowing the lungs 100 and the trachea 110 to be stimulated. In one exemplary application, the vibration-generating devices would be held in contact with the thorax by an adjustable belt 145. In still another exemplary application, the vibration-generating devices would be attached to the back or side of a chair, and the thorax positioned such that direct contact is maintained with the vibration generators.

Since each patient generally responds differently to external vibrational stimuli, control means are required to regulate these stimulations, such that the vibrations transmitted to the pulmonary system are effective in increasing the mobility of the mucus attached to the lungs 100 and trachea 110 without causing undue stress to the patient. This will depend both on the degree of mucus congestion, and on the mechanical properties of the lungs 100 and rib cage 120. For example, the lung resonant frequency of a small child will be approximately twice that of an adult. Furthermore, the lung resonant frequency will generally be significantly different when the lungs 100 are congested with mucus. A second physical difference between patients is the rib-cage resonant frequency, which has an important influence on the efficacy of the vibrational stimulations. Since the lungs 100 can be vibrated both directly, and indirectly as a response to vibration of the rib cage 120, mucus loosening will benefit from both types of excitation. Also, generally, for a given spectral content of the vibrational energy transmitted to the thorax, efficacy of mucus clearance from the lungs 100 and trachea 110 will depend directly on the intensity of the vibrations, which should be subject to regulation by the patient or caregiver to achieve the desired benefit without undue stress.

Regulation of the vibrational stimulations is achieved by employing a portable control console 25 operated by the patient or caregiver. This would generally include the ability to regulate the vibration spectrum applied to the thorax, as well as the intensity of the vibrations. It is also important that the patient or caregiver be given the means to terminate the vibrational excitations, both as a safety measure, and to allow the patient time to rest or cough. Application of vibration during the inspiration phase of the breathing cycle may also be undesirable for some patients, and could be discontinued during this part of the respiratory cycle.

The application of vibration to the pulmonary system causes a significant increase in the mobility of the mucus attached to the lungs 100 and trachea 110; however, in itself, the vibration has little potential for expelling mucus from the pulmonary system. To accomplish the latter, a second type of excitation is required which applies compressive stimulations to the lower thorax, inducing a series of huffs. Application of compressive stimulations to the lower-thoracic region can be achieved by various means. In one exemplary application, an electromechanical actuator would be used to apply compressive forces directly to the thorax. In still another exemplary application, the compressive stimulations would be transmitted by means of one or more inflatable bladders held against the thorax by an adjustable belt 155, and pressurized by a controlled source of pneumatic pressure. In yet another exemplary application, the compressive stimulations would be transmitted by means of a single inflatable cuff or belt, secured around the lower thorax, and pressurized by a controllable source of pneumatic pressure As in the case of the vibrational stimulations, the compressive stimulations need to be controlled to reflect patient-specific requirements, and to achieve overall efficacy without discomfort to the patient. The objective of the control scheme is to regulate the compressions of the lower-thoracic region in a manner which creates simultaneous increases in the pressure and expiration rate of air contained within the lungs 100 and trachea 110, thereby leading to a series of huffs. Then, together with concurrent application of the vibrational stimulations, the compressive stimulations will cause the desired incremental movements of the mucus along the lung and tracheal walls. Generally, compressive stimulations would be applied only during the expiration phase of the respiratory cycle, and inhibited by the patient or caregiver during the inspiration phase. The control console 25 provides the means by which the patient or caregiver may regulate the compressive stimulations to the lower thorax.

PREFERRED EMBODIMENT OF THE INVENTION

Efficacious clearance of mucus from the pulmonary system is based upon the principle disclosed in the previous section. The principle states that vibratory stimulations should be applied to the thorax to loosen the mucus and, concurrently, compressive stimulations should be applied to the lower thorax to create the motive forces necessary to propel the mucus in incremental steps toward the mouth, where it can be swallowed or expectorated.

For some subjects, depending on body type, the therapeutic benefit would be optimized by administering concurrent vibratory and compressive stimulations at separate sites on the thorax during a therapy session, with the lower-thoracic region being essential for administering the compressive stimulations. For other subjects, the therapeutic benefit would be optimized by the concurrent application of both vibratory and compressive stimulations at a single lower-thoracic site during a therapy session.

Various mechanization approaches may be used to implement the vibratory and compressive pressure stimulations, each having unique safety, adaptability and cost characteristics. From a safety perspective, pneumatic stimulation has an advantage in that no electrified elements are in contact with the body. Furthermore, there is a greater ability to prevent bodily injury from a runaway actuator when pneumatic pressure is utilized as the source of the stimulations. The adaptability of the device, defined as its ability to effectively satisfy a spectrum of user needs, will generally differ from one implementation to another. Typically, there will be a tradeoff between the cost of the device and its adaptability. For example, cost may be reduced if the device is limited to a single composite stimulation, consisting of vibratory and compressive components, applied to the lower-thoracic region. However, from an adaptability perspective, doing so may impose an undesirable restriction for some users.

Figure 2:
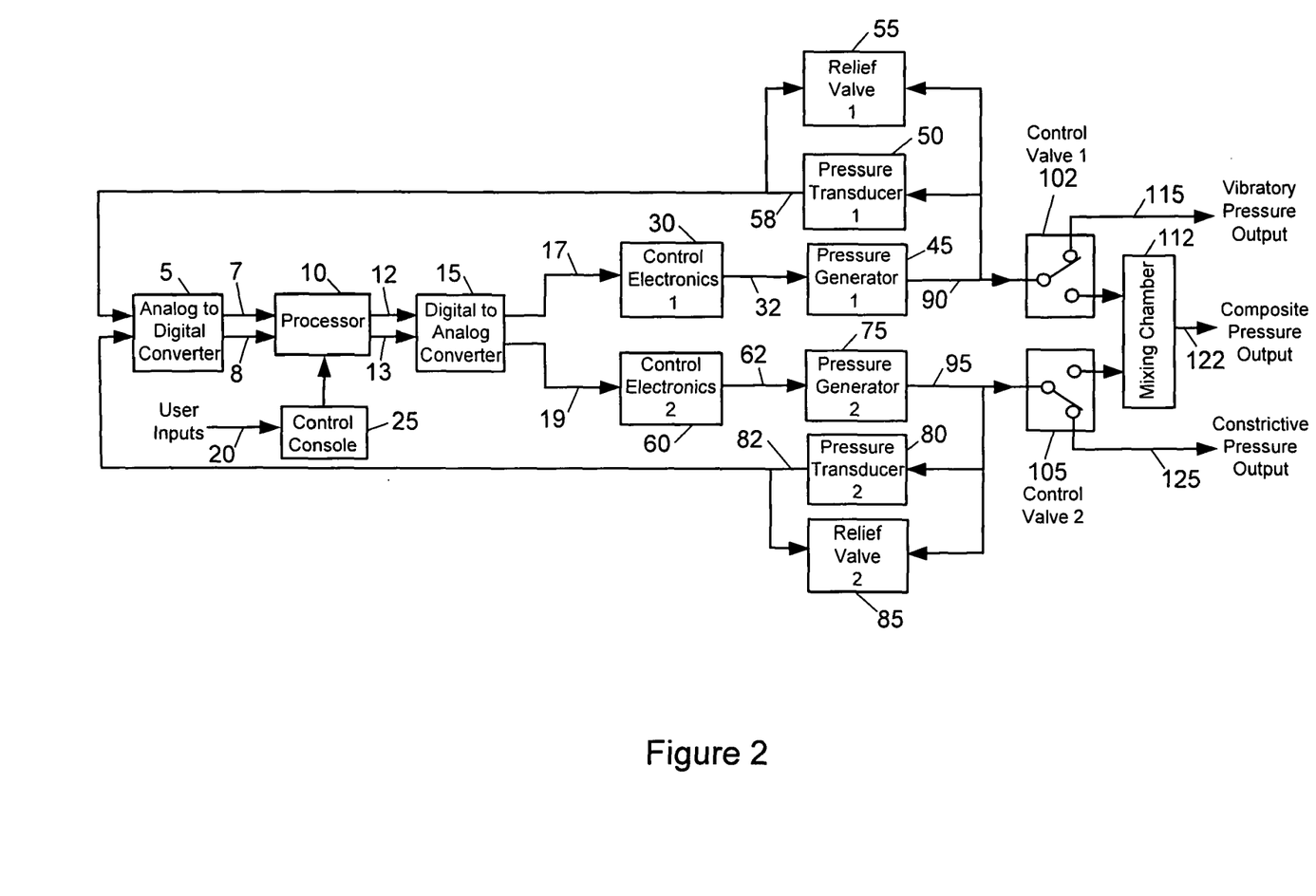
FIG. 2 shows a generalized block diagram of a device for generating vibratory and constrictive pressure outputs or, alternatively, a composite pressure output consisting of vibratory and constrictive components.

The preferred embodiment of the invention allows individual vibratory and compressive stimulations to be provided at separate sites on the thorax, as well as a composite stimulation consisting of vibratory and compressive components to be provided to the lower-thoracic region, thereby insuring maximum adaptability. FIG. 2 defines a generalized mechanization diagram for this preferred embodiment. The system consists of two pneumatic pressure generators, pressure generator 1 45 and pressure generator 2 75, which create time-varying output-pressure variations. Pressure generator 1 45 creates a high-frequency vibratory pressure variation, and pressure generator 2 75 creates a low-frequency compressive pressure variation, hereafter referred to as a constrictive pressure variation. In one exemplary application, the pressure generators would be implemented using an air compressor to maintain a controlled source of pneumatic pressure within a pressure vessel, together with a set of spool valves in communication with the pressure vessel and the atmosphere for controlling the input and venting of the air within the two pressure generators. In still another exemplary application, the pressure generators would be implemented using air cylinders which act like piston pumps to create the desired time-varying pressure variations.

Pressure transducer 1 50 monitors the pressure in pressure generator 1 45, and pressure transducer 2 80 monitors the pressure in pressure generator 2 75. This provides the means for maintaining closed-loop control of the system, and insures that any system failure which causes an excessive pressure level will be quickly detected. Relief valve 1 55 and relief valve 2 85 are used to dissipate the pressure applied to the body if an unsafe pressure level has been detected via pressure transducer 1 50 or pressure transducer 2 80.

An analog-to-digital converter 5 is used to acquire an analog signal 58 from pressure transducer 1 50 and an analog signal 82 from pressure transducer 2 80, and to generate digital input signals 7 and 8 to the processor 10. The processor 10, in turn, outputs digital signals 12 and 13 to a digital-to-analog converter 15, which provides an analog drive signal 17 to control electronics 1 30 and an analog drive signal 19 to control electronics 2 60. Control electronics 1 30 generates an electrical activation signal 32 for pressure generator 1 45, and control electronics 2 60 generates an electrical activation signal 75 for pressure generator 2 75. The processor 10 hosts the necessary algorithms to implement the control laws required to maintain closed-loop control of the system.

The output pressure 90 of pressure generator 1 45 and the output pressure 95 of pressure generator 2 75 are individually available to a user as a vibratory pressure output 115 and a constrictive pressure output 125, depending on the configurations of control valve 1 102 and control valve 2 105. In another configuration of control valve 1 102 and control valve 2 105, the output pressure 90 of pressure generator 1 45 and the output pressure 95 of pressure generator 2 75 are superimposed in a mixing chamber 112 so that a composite pressure output 122 is available to the user.

The ability to set up different pressure outputs is carried out using a control console 25. The control console 25 is activated by the user or caregiver via a set of user inputs 20, and has a plurality of accessible control settings, whereby a desired vibratory pressure variation and a desired constrictive pressure variation may be specified. For the vibratory pressure variation, the control settings allow the amplitude and frequency characteristics to be selected. For the constrictive pressure, the control settings allow the temporal characteristics of the variation to be selected, which could be defined by an amplitude and frequency, or by an amplitude, rise time, duration and decay time.

In the therapeutic application of interest, one or more air hoses would typically be used to convey the air pressures generated by the apparatus to one or more suitably chosen pressure receivers held in contact with the thorax by one or more non-extensible belts, whereby concurrent application of the vibratory and constrictive pressure stimulations cause the mucus to be expelled from the pulmonary system.

Figure 3:
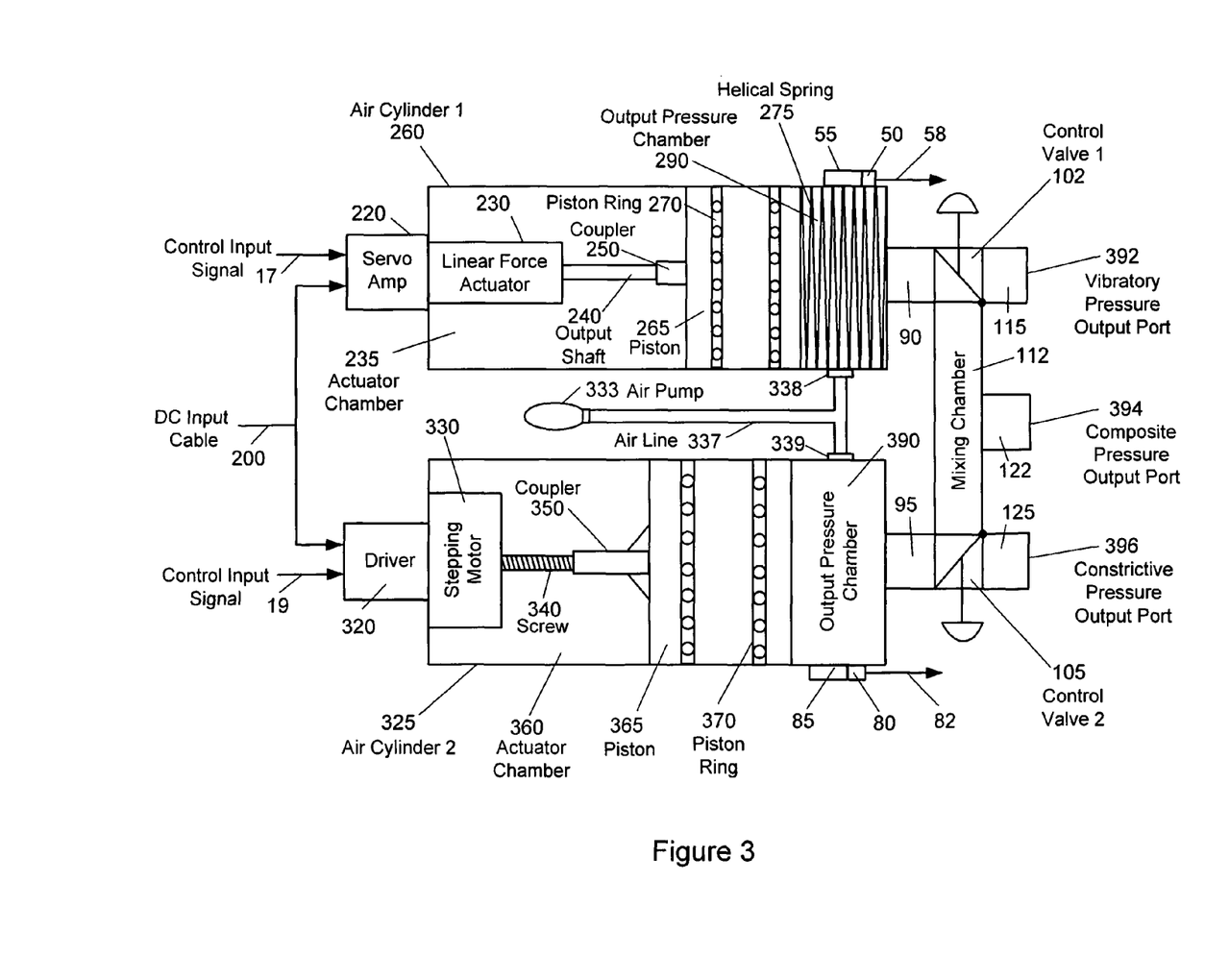
FIG. 3 shows a mechanization diagram for a preferred embodiment of the vibratory, constrictive and composite pressure-generation functions.

FIG. 3 is a detailed mechanization diagram for implementing the vibratory, constrictive and composite pressure-generation functions. In this preferred embodiment, the system consists of two air cylinders, air cylinder 1 260 and air cylinder 2 325, which function as piston pumps to create the desired time-varying output pressure variations. As shown, the actuators are contained within the air cylinders, as opposed to being externally located, which is a distinct option within the preferred embodiment.

Air cylinder 1 260 creates the desired high-frequency vibratory pressure variation in its output pressure chamber 290 when its piston 265 executes forced oscillations at a specified frequency. This is accomplished using a linear force actuator 230 to apply a periodic force to the piston 265, together with a helical spring 275 connected to the cylinder housing and piston, which applies a restoring force. The air contained within the cylinder output pressure chamber 290 acts like an air spring, and also provides a restoring force. The output of the linear force actuator 230 is transmitted to the piston 265 via an output shaft 240 and coupler 250. A servo amplifier 220 generates an electric current input to the linear force actuator 230 which, in turn, applies an oscillatory force to the piston 265. The resultant oscillatory motion of the piston 265 leads to an oscillatory variation in the volume of the cylinder's output pressure chamber 290, which results in the desired vibratory pressure variation. Piston rings 270 allow the piston 265 to operate with a minimum of friction, and also provide a seal between the actuator chamber 235 and the output pressure chamber 290. The linear force actuator may be chosen from a number of available types, among which are linear motor, moving-coil actuator and moving-magnet actuator. The control signal input 17 to the servo amplifier 220 activates the linear force actuator 230. The servo amplifier 220 receives a source of DC power from a DC input cable 200, which conveys the DC output of an included AC to DC converter. A cable from a standard AC wall outlet to the AC to DC converter is also assumed Air cylinder 2 325 creates a desired low-frequency constrictive pressure variation in its output pressure chamber 390 when its piston 365 executes a prescribed translational motion. This is accomplished using a stepping motor 330 to cause the piston 365 to undergo translational motion. The motion of the piston varies the volume of the output pressure chamber 390 which, in turn, results in the desired constrictive pressure variation. The stepping motor output consists of a series of discrete incremental-angle rotations, each of which causes an incremental rotation of a screw 340. Incremental rotations of the screw 340 are converted into incremental translational motions of the piston 365 via a coupler 350. Piston rings 370 allow the piston 365 to operate with a minimum of friction, and also provide a seal between the actuator chamber 360 and the output pressure chamber 390. A driver 320 generates the necessary voltage commands to the stepping motor 330 which, in turn, positions the piston 365 via rotation of the screw 340. The screw 340 can take the form of a lead screw, an acme screw or a ball screw. The control input signal 19 to the driver 320 controls the stepping motor 330. The driver receives a source of DC power from the DC input cable 200.

Control valve 1 102 and control valve 2 105 are used to select the pressure outputs of the device. Depending on the position of control valve 1 102, the vibratory output pressure 90 of air cylinder 1 260 may be channeled either to the vibratory pressure output port 392 or to the mixing chamber 112. Similarly, the position of control valve 2 105 allows the constrictive output pressure 95 of air cylinder 2 325 to be channeled either to the constrictive pressure output port 396 or to the mixing chamber 112. When both the vibratory pressure output 90 and the constrictive pressure output 95 are channeled to the mixing chamber 112, a composite pressure output is available at the composite pressure output port 394.

FIG. 3 also shows an optional air pump 333 for creating a desired quiescent pressure in the output pressure chamber 290 of air cylinder 1 260 and in the output pressure chamber 390 of air cylinder 2 325. The air pump 333 can be activated manually, or by means of a small air blower. A one-way valve 338 is used in air cylinder 1 260 to prevent air escape, and a second one-way valve 369 is used in air cylinder 2 325 for the same purpose. An air line 337 connects the air pump 333 and the output pressure chamber 290 of air cylinder 1 260 and the output pressure chamber 390 of air cylinder 2 325.

The physical characteristics of the two pressure generators are chosen such that air cylinder 1 260 generates vibratory pressure variations having a spectral content substantially contained within the frequency range 5 to 20 Hz, and air cylinder 2 325 generates constrictive pressure variation having a spectral content substantially contained within the frequency range 0 to 5 Hz. These frequency ranges are chosen to maximize the potential of the device to provide a useful repertoire of therapeutic stimulations while, at the same time, recognizing practical design constraints.

In applying therapeutic pressure stimulations to humans, both children and adults, safety must be guaranteed. This necessitates precise control, with the ability to terminate the pressure stimulations if an unsafe level arises. Also, efficacy of the therapy requires that the stimulations be well articulated. To achieve both safety and efficacy, a closed-loop approach is required. This, in turn, requires continuous pressure monitoring, together with a set of real-time control algorithms for generating control signals to the actuators. Closed-loop control allows the pressure variations transmitted to the pressure receivers to be regulated in a manner which insures that the desired pressure stimulations to the body are achieved in a safe and predicable manner. Contemporary digital processor technology allows sophisticated real-time closed-loop control algorithms to be implemented.

Figure 4:
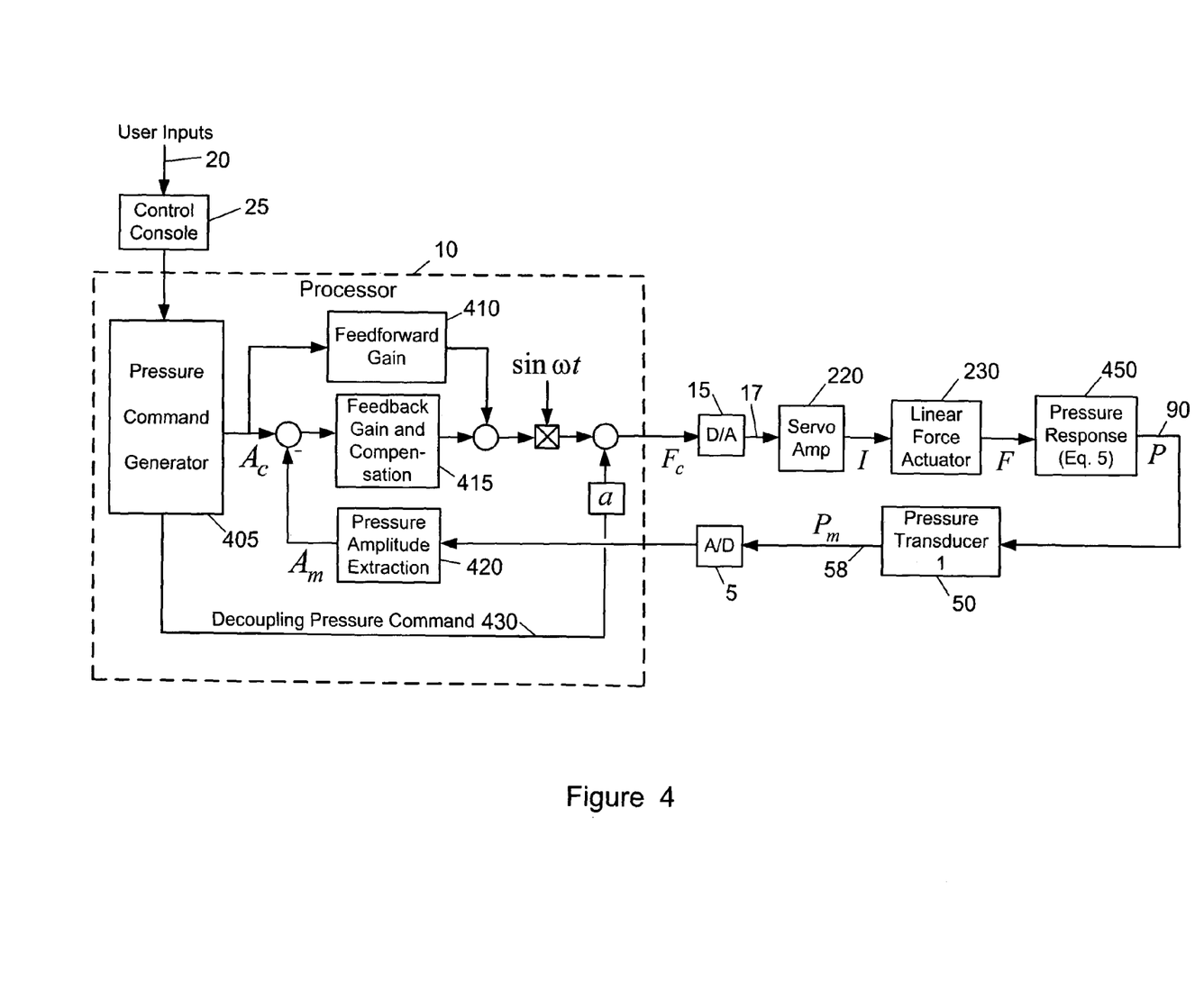
FIG. 4 shows a block diagram for implementing closed-loop control of the vibratory pressure-generation function in the preferred embodiment.
Figure 5:
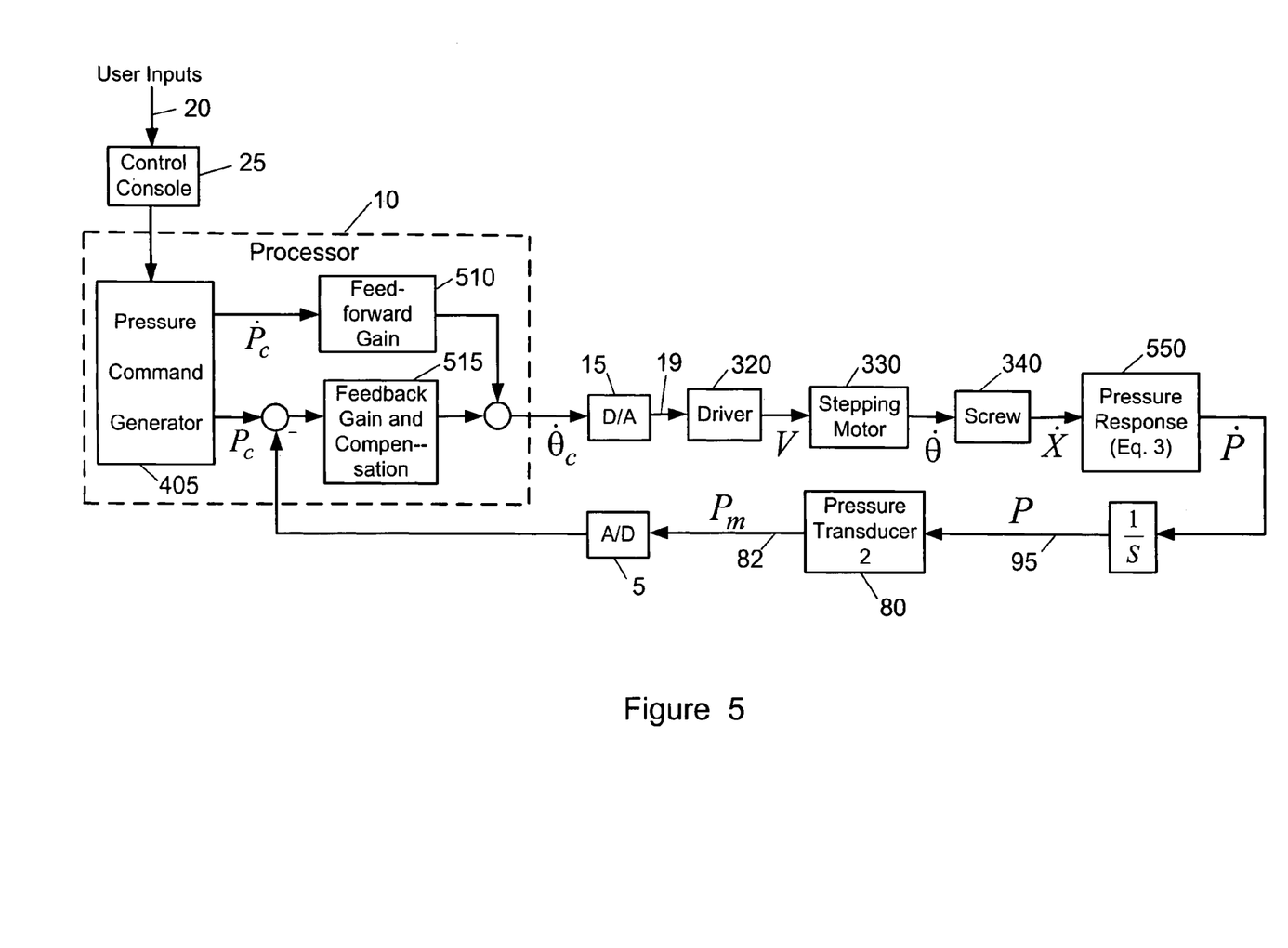
FIG. 5 shows a block diagram for implementing closed-loop control of the constrictive pressure-generation function in the preferred embodiment.

FIGS. 4 and 5 provide block diagrams for implementing closed-loop control of air cylinder 1 260 and air cylinder 2 325, respectively. A basic principle utilized in both control schemes is Boyle's Gas Law for a confined gas. From Boyle's Gas Law, the following relationship is true $$PV^\gamma = \text{constant} \quad (1)$$

where P is gas pressure, V is gas volume, and γ is a constant ranging from 1.0 for isothermal expansion/contraction to 1.4 for adiabatic expansion/contraction. In the present application, the confined gas volume consists of the combined volume of the cylinder output pressure chamber, connecting hose and pressure receiver.

The incremental pressure to incremental stroke gain for the cylinder pressure output chamber, connecting hose and pressure receiver combination may be derived directly from (1), and is given by:

$$\frac{\Delta P}{\Delta x} = K_p = \frac{\gamma A P}{\gamma c P + V_0 (P_0/P)^{1/\gamma}} \quad (2)$$

where
  Δx=incremental piston stroke
  ΔP=incremental cylinder output pressure
  A=piston area
  c=composite compliance coefficient for the pressure receiver and area of pressure application on the body
  $V_0$=quiescent volume of pressure output chamber, hose and pressure receiver
  $P_0$=quiescent pressure of pressure output chamber, hose and pressure receiver and the quiescent pressure and volume are understood to be the corresponding values of P and V when the piston is in its starting position. The incremental pressure to incremental stroke gain, $K_p$, is a fundamental parameter in each of the two control schemes. Another useful form of (2) is the following:

$$\frac{\dot{P}}{\dot{x}} = K_p \quad (3)$$

where
  $\dot{P}$=rate of change cylinder output pressure
  $\dot{x}$=rate of change of piston stroke and $K_p$ is as defined in (2). Equation (3) defines the pressure response transfer function utilized in the constrictive pressure control concept illustrated in FIG. 5.

For air cylinder 1 260, a transfer function relating the translational motion of the piston to the applied force is required. This transfer function is based on a force balance for the piston 265, including the restraining effect of the helical spring 275 together with the restraining effect of the air entrapped in the cylinder output pressure chamber, hose and pressure receiver. The relevant transfer function is defined as follows:

$$x(s) = \left(\frac{1}{ms^2 + fs + k + aK_p}\right) F(s) \quad (4)$$

where the following definitions apply
  x(s)=piston linear translation
  F(s)=force applied to piston
  $K_p$=incremental pressure to incremental stroke gain
  k=spring rate of helical spring
  a=area of piston in air cylinder 1
  m=mass of piston, actuator output shaft and coupler
  f=damping force coefficient, resulting from viscous friction and actuator back emf
  s=Laplace complex operator A transfer function relating the pressure output to the force input may then be defined by $$P(s) = \left(\frac{K_p}{ms^2 + fs + k + aK_p}\right) F(s) \quad (5)$$

where P(s) is the output pressure of air cylinder 1 260. The transfer function given by (5) defines the pressure response transfer function appearing in FIG. 4. This transfer function, in turn, provides the basis for a transfer function relating the amplitude of the output pressure to the amplitude of the force input, which is as follows:

$$A_p(\omega) = \left(\frac{K_p}{[(k + aK_p - m\omega^2)^2 + f^2\omega^2]^{1/2}}\right) A_F(\omega) \qquad (6)$$

where $A_p$=amplitude of the vibratory pressure output
$A_F$=amplitude of the force input
$\omega$=angular rate of the vibratory pressure output The relationships defined by Equations (1) through (6) are based on fundamental pneumatic principles discussed in detail in: "The Analysis and Design of Pneumatic Systems, by B. W. Andersen, Krieger Publishing Company, 2001, ISBN 1-57524-164-1, and elsewhere.

Referring to FIG. 4, it is seen that the software embedded in the processor generates an oscillatory command signal to the linear force actuator consisting of the sum of a feedforward component and a feedback component. A biasing command signal is also incorporated into the total command signal to the linear force actuator 230. The biasing signal defines a time-varying component which decouples the vibratory and constrictive pressures. The decoupling command signal 430 is used when a composite output pressure variation is desired.

The benefit of using a feedforward control signal is that pressure control is more accurate and robust in the presence of nonlinearities and uncertainty in the parameter $K_p$, which follows from the fact that the actuator is effectively controlled by the feedforward signal, and only a limited amount of correction needs to be provided by the feedback control loop. This allows the bandwidth of the feedback control loop to be maintained at a low value, thereby greatly alleviating stability issues that could potentially arise from parameter uncertainties, nonlinearities and unmodeled high-frequency effects.

The software modules embedded in the processor 10 for controlling the vibratory pressure variation in air cylinder 1 260 are defined in greater detail in the following paragraphs.

The pressure command generator 405 outputs a commanded amplitude, $A_c$, for the vibratory pressure, together with a decoupling pressure command 430. The decoupling pressure command is equal to the commanded value of the constrictive pressure variation in air cylinder 2 325.

The pressure amplitude extraction module derives the amplitude of the vibratory pressure variation from the pressure measured by the pressure transducer 1 50.

The feedforward gain module 410 generates a control signal which is directly proportional to the commanded amplitude of the vibratory pressure variation, and inversely proportional to the nominal ratio of the pressure amplitude to force amplitude at a specified vibratory frequency for air cylinder 1 260.

The feedback gain and compensation module 415 generates a control signal which is directly proportional to the difference between the commanded amplitude of the vibratory pressure variation and the actual amplitude, $A_m$, as measured by pressure transducer 1 50, and extracted by the pressure amplitude extraction module 420. The feedback gain and compensation module 415 would also typically incorporate a roll-off filter to reduce feedback loop responsiveness at high frequencies.

An operation is included for multiplying the sum of the feedforward control signal and feedback control signal by a unity-amplitude sine wave having a frequency equal to the desired frequency, $\omega$, of the vibratory pressure variation, to yield a total force command signal to the linear force actuator 230.

An operation is included for multiplying the decoupling command signal by the cross-sectional area, a, of the piston 265, to yield a command augmentation signal to the linear force actuator.

An operation is included to add the command augmentation signal to the total command signal, to yield an augmented total command signal, $F_c$, to the linear force actuator 230. The augmented total force command signal is converted via the digital-to-analog converter 15 into an analog voltage 17 input to the servo amp 220 which, in turn, generates a current, I, to the linear force actuator 230. The force, F, generated by the linear force actuator causes the volume of the output pressure chamber 290 to vary, thereby leading to the vibratory pressure variation 90. The vibratory pressure, P 90, is measured by pressure transducer 1 50 as $P_m$ 58, which is converted by the analog-to-digital converter 5 into a digital signal for use in the pressure amplitude extraction module 420, thereby resulting in the derived vibratory pressure amplitude, $A_m$.

FIG. 5 illustrates the control scheme for air cylinder 2 325. The control signal to the stepping motor 330 consists of the sum of a feedforward component and a feedback component. The feedforward control positions the piston 365 in air cylinder 2 in a manner which approximately produces the desired instantaneous constrictive pressure. As is true for air cylinder 1, a significant benefit accrues from the use of feedforward control, due to the fact that the actuator is effectively controlled by the feedforward signal, and only a limited amount of correction needs to be provided by the feedback control loop. This allows the bandwidth of the feedback control loop to be maintained at a low value to minimize stability problems associated with parameter uncertainties, nonlinearities and unmodeled high-frequency effects.

The software modules embedded in the processor 10 for controlling the constrictive pressure variation in air cylinder 2 325 are defined in greater detail in the following paragraphs.

The feedforward gain module 510 generates a feedforward control signal which is directly proportional to the commanded rate of change, $\dot{P}_c$, of the constrictive pressure variation, and inversely proportional to the nominal ratio of incremental pressure to incremental stroke for the output pressure chamber 390, hose and pressure receiver. The feedforward control signal is also inversely proportional to screw pitch.

The feedback gain and compensation module 515 is included for generating a feedback control signal to the stepping motor which is proportional to the difference between the commanded constrictive pressure variation profile, $P_c$, and the actual pressure variation profile measured by pressure transducer 2 80. The feedback gain and compensation module 515 would also typically incorporate a roll-off filter to reduce feedback loop responsiveness at high frequencies.

An operation is included for adding the feedback control signal and the feedforward control signal to yield a total angular rate command signal, $\dot{\theta}_c$, consisting of a sequence of incremental stepping motor output shaft angular rotations. The angular rate command is converted, via the digital-to-analog converter 15, to an analog voltage signal 19 to the driver 320 which, in turn, generates a set of voltages, V, to the stepping motor 330. The resulting angular rate, $\dot{\theta}$, of the stepping motor output shaft 240 is converted to a linear motion, $\dot{X}$, by the screw 340 which establishes, via its pitch, the ratio of incremental linear motion to incremental shaft rotation. The linear motion of the screw 340 is transmitted to the piston 365 in air cylinder 2 325 which, in turn, varies the volume of the output pressure chamber 390, thereby leading to the constrictive pressure output pressure variation 95. The constrictive pressure, P 95, is measured by pressure transducer 2 80 as $P_m$ 82, which is converted by the analog-todigital converter 5 into a digital signal for use in the feedback gain and compensation module 515 in the processor 10.

The embodiments described herein are sufficiently detailed to allow those skilled in the arts to practice the claimed invention, and it is understood that other embodiments may be utilized without departing from the true nature of the claimed invention

What is claimed is:

1. An apparatus for clearing mucus from the pulmonary system of a human, comprised of:
   first pneumatic pressure generator providing a source of vibratory pressure variations to the thorax of said human, whereby said vibratory pressure variations cause vibrations to develop in the pulmonary system comprised of the lungs and trachea of said human in use;
   first control means to regulate intensity and frequency of said vibratory pressure variations, whereby the mobility of mucus attached to said lungs and trachea is increased in use;
   second pneumatic pressure generator providing a source of constrictive pressure variations to said thorax of said human, whereby said constrictive pressure variations cause compressions of the lower-thoracic region comprised of the abdominal wall and thoracic diaphragm of said human in use;
   second control means to regulate intensity and frequency of said constrictive pressure variations, whereby said compressions of said lower-thoracic region cause expiration of air contained within said lungs and trachea in use; and
   a processor for implementing said first and said second control means;
   whereby concurrent application to said thorax of said vibratory and said constrictive pressure variations, via at least one air hose, and at least one pressure receiver held in external contact with said thorax, causes movement of said mucus from said pulmonary system of said human in use.

2. The apparatus of claim 1, further comprised of:
   a first air cylinder containing a first piston which undergoes oscillatory motion, whereby said oscillatory motion of said first piston produces said vibratory pressure variations in the pressure output of said first air cylinder.

3. The apparatus of claim 2, further comprised of:
   a linear force actuator which generates an oscillatory force, said oscillatory force being transmitted to said first piston via said a mechanical linkage connecting said first piston and said linear force actuator; and
   drive electronics for generating an oscillatory current input to said linear force actuator.

4. The apparatus of claim 1 further comprised of:
   an air cylinder containing a piston which undergoes translational motion, whereby said translational motion of said piston produces said constrictive pressure variations in the pressure output of said air cylinder.

5. The apparatus of claim 4, further comprised of:
   an electrical motor which generates angular motions of its output shaft, said angular motions being converted to translational motions of said piston by a mechanical linkage connecting said piston to said electrical motor output shaft; and
   drive electronics for generating voltage inputs to said electrical motor.

6. The apparatus of claim 1, further comprised of:
   control input means, activated by a user or caregiver, allowing a desired vibratory pressure variation to be specified;
   a first pressure transducer providing a measurement of said vibratory pressure variations;
   a set of control algorithms embedded in said processor to derive a digital command signal for a first linear force actuator that produces the vibratory pressure variations, the digital command signal based upon a digital realization of said first pressure transducer measurement and said desired vibratory pressure variation;
   digital to analog converter means for generating an analog voltage realization of said linear force actuator digital command signal; and
   analog to digital converter means for generating said digital realization of said first pressure transducer measurement.

7. The apparatus of claim 6, further comprised of:
   a software module for deriving the amplitude of said vibratory pressure variations from the pressure measured by said first pressure transducer;
   a software module for generating a first feedforward control signal, said first feedforward control signal being directly proportional to a desired amplitude of said vibratory pressure variations, and inversely proportional to a nominal ratio of pressure amplitude to force amplitude at a specified frequency for a first cylinder for producing the vibratory pressure variations;
   a software module for generating a first feedback control signal, said first feedback control signal being directly proportional to the difference between said desired amplitude of said vibratory pressure variations and an amplitude of said vibratory pressure variations measured by said first pressure transducer; and
   a software module for multiplying the sum of said first feedforward control signal and said first feedback control signal by a unity-amplitude sine wave having a frequency equal to a desired frequency of said vibratory pressure variations, thereby yielding a total force command signal to said linear force actuator.

8. The apparatus of claim 1, further comprised of:
   control input means, activated by user or caregiver, allowing a desired constrictive pressure variation to be specified;
   a pressure transducer providing a measurement of said constrictive pressure variations;
   a set of control algorithms embedded in said processor to derive a digital command signal for an electric motor that produces the constrictive pressure variations, the digital command signal based upon a digital realization of said pressure transducer measurement and said desired constrictive pressure variation;
   digital to analog converter means for generating an analog voltage realization of said electric motor digital command signal; and
   analog to digital converter means for generating said digital realization of said second pressure transducer measurement.

9. The apparatus of claim 8, further comprised of:
   a software module for generating a feedforward control signal, said feedforward control signal being directly proportional to a rate of change of said desired constrictive pressure variations, and inversely proportional to a nominal ratio of incremental pressure to incremental stroke for an air cylinder producing said constrictive pressure variations;
   a software module for generating a feedback control signal, said feedback control signal being directly proportional to the difference between the said desired constrictive pressure variations and pressure measured by the pressure transducer; and a software module for adding said feedforward control signal and said feedforward control signal, thereby yielding a total command signal to said electrical motor.

10. The apparatus of claim 1, further comprised of:
pressure combining means, whereby said vibratory and said constrictive pressure variations are combined into a single composite pressure variation, said composite pressure variations having the individual temporal characteristics of said vibratory and said constrictive pressure variations.

11. The apparatus of claim 10, further comprised of:
a mixing chamber for superimposing said vibratory and said constrictive pressure variations, said mixing chamber having at least one output port allowing transmission of said composite pressure variation to said human; and
pressure decoupling means to decouple the generation of said vibratory pressure variations from the generation of said constrictive pressure variations.

12. The apparatus of claim 11, further comprised of:
pressure selection means, whereby pressure output of the apparatus may be chosen from one of: said vibratory pressure variations and said constrictive pressure variations, as separate entities; or said composite pressure variation.

13. The apparatus of 12, further comprised of:
at least one control valve allowing said pressure output of the apparatus to be selected by a user or caregiver.

14. An apparatus for clearing mucus from the pulmonary system of a human, comprised of:
a pneumatic pressure generator which provides a source of:
vibratory pressure variations to the lower-thoracic region of a human, comprised of the abdominal wall and thoracic diaphragm of said human, whereby said vibratory pressure variations cause vibrations to develop in the pulmonary system comprised of the lungs and trachea of said human in use, and
constrictive pressure variations to said lower-thoracic region of said human, whereby said constrictive pressure stimulations cause compressions of said lower-thoracic region of said human in use;
first control means to regulate intensity and frequency of said vibratory pneumatic pressure variations, whereby said vibrations cause the mobility of mucus-attached to said lungs and trachea to be increased in use;
second control means to regulate intensity and frequency of said constrictive pneumatic pressure variations, whereby said compressions of said lower-thoracic region cause expiration of air contained within said lungs and trachea in use; and
a processor for implementing said first and said second control means;
whereby concurrent application to said lower-thoracic region of said vibratory and said constrictive pressure variations, via at least one air hose, and at least one pressure receiver held in external contact with said lower-thoracic region causes movement of said mucus from said pulmonary system of said human in use.

15. The apparatus of claim 14 further comprised of:
an air cylinder containing a piston which undergoes translational motion in response to a linear force actuator, whereby said translational motion of said piston produces said vibratory and said constrictive pressure variations in the pressure output of said air cylinder; and
a mechanical linkage connecting said linear force actuator to said piston.

* * * * *